US010482598B2

(12) United States Patent
Nakagawa et al.

(10) Patent No.: US 10,482,598 B2
(45) Date of Patent: *Nov. 19, 2019

(54) CELL ANALYSIS SYSTEM, CELL ANALYSIS PROGRAM AND CELL ANALYSIS METHOD

(71) Applicant: Sony Corporation, Tokyo (JP)

(72) Inventors: Kazuhiro Nakagawa, Saitama (JP); Takuya Kishimoto, Tokyo (JP); Eriko Matsui, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/188,151

(22) Filed: Nov. 12, 2018

(65) Prior Publication Data

US 2019/0080452 A1 Mar. 14, 2019

Related U.S. Application Data

(63) Continuation of application No. 15/033,089, filed as application No. PCT/JP2014/004804 on Sep. 18, 2014, now Pat. No. 10,163,203.

(30) Foreign Application Priority Data

Nov. 8, 2013 (JP) .................................. 2013-232444

(51) Int. Cl.
*G06K 9/00* (2006.01)
*G06T 7/00* (2017.01)
(Continued)

(52) U.S. Cl.
CPC .......... *G06T 7/0012* (2013.01); *C12M 41/46* (2013.01); *G01N 33/5029* (2013.01);
(Continued)

(58) Field of Classification Search
CPC ............ C12M 41/46; G01N 2333/705; G01N 33/5029; G01N 33/5035; G01N 33/6872;
(Continued)

(56) References Cited

U.S. PATENT DOCUMENTS 7,246,012 B2 7/2007 Kutsyy et al.
8,668,647 B2 3/2014 Eskandari et al.
(Continued)

FOREIGN PATENT DOCUMENTS

EP 2562533 A1 2/2013
JP 2003-527113 A 9/2003
(Continued)

OTHER PUBLICATIONS

International Search Report and Written Opinion and English translation thereof dated Dec. 24, 2013 in connection with Application No. PCT/JP2013/006646.

(Continued)

*Primary Examiner* — Tom Y Lu
(74) *Attorney, Agent, or Firm* — Wolf, Greenfield & Sacks, P.C.

(57) ABSTRACT

A cell analysis system according to the present disclosure includes a motion information extracting unit and a motion characteristics calculating unit. The motion information extracting unit extracts motion information arising from a movement of ions or molecules across a cell membrane, out of a cell image obtained from imaging a cell in time series. The motion characteristics calculating unit calculates motion characteristics of the motion information.

16 Claims, 9 Drawing Sheets

(51) Int. Cl.
C12M 1/34 (2006.01)
G01N 33/50 (2006.01)
G01N 33/68 (2006.01)
G06T 7/20 (2017.01)

(52) U.S. Cl.
CPC ..... *G01N 33/5035* (2013.01); *G01N 33/6872* (2013.01); *G06T 7/20* (2013.01); *G01N 2333/705* (2013.01); *G06T 2207/30024* (2013.01)

(58) Field of Classification Search
CPC ......... G06T 2207/30024; G06T 7/0012; G06T 7/20
See application file for complete search history.

(56) References Cited

U.S. PATENT DOCUMENTS

| | | | |
|---|---|---|---|
| 8,712,139 | B2 | 4/2014 | Rittscher et al. |
| 10,163,203 | B2* | 12/2018 | Nakagawa ............ G06T 7/0012 |
| 10,209,236 | B2 | 2/2019 | Nakagawa et al. |
| 2006/0014137 | A1 | 1/2006 | Ghosh et al. |
| 2006/0216688 | A1 | 9/2006 | Maher et al. |
| 2006/0216689 | A1 | 9/2006 | Maher et al. |
| 2006/0216690 | A1 | 9/2006 | Maher et al. |
| 2007/0054266 | A1 | 3/2007 | Sato et al. |
| 2007/0294778 | A1 | 12/2007 | Rich |
| 2008/0304732 | A1 | 12/2008 | Rittscher et al. |
| 2009/0196482 | A1 | 8/2009 | Kobayashi et al. |
| 2009/0202130 | A1 | 8/2009 | George et al. |
| 2010/0209934 | A1 | 8/2010 | Oh et al. |
| 2012/0149052 | A1 | 6/2012 | Grohovaz et al. |
| 2013/0070971 | A1 | 3/2013 | Kunihiro et al. |
| 2013/0088719 | A1 | 4/2013 | Sugiyama et al. |
| 2013/0224756 | A1 | 8/2013 | Cohen |
| 2013/0321459 | A1 | 12/2013 | Hayakawa et al. |
| 2013/0344559 | A1 | 12/2013 | Engeberg et al. |
| 2016/0041144 | A1 | 2/2016 | Nakagawa et al. |
| 2016/0282338 | A1 | 9/2016 | Miklas et al. |
| 2016/0284081 | A1 | 9/2016 | Nakagawa et al. |
| 2017/0069860 | A1 | 3/2017 | Zorlutuna |
| 2017/0246148 | A1 | 8/2017 | Kil |

FOREIGN PATENT DOCUMENTS

| | | | |
|---|---|---|---|
| JP | 2004-008173 | A | 1/2004 |
| JP | 2006-184207 | A | 7/2006 |
| JP | 2006-525210 | A | 11/2006 |
| JP | 2006-526389 | A | 11/2006 |
| JP | 2006-329672 | A | 12/2006 |
| JP | 2008-538287 | A | 10/2008 |
| JP | 2009-118817 | A | 6/2009 |
| JP | 2010-538603 | A | 12/2010 |
| JP | 2011-122953 | A | 6/2011 |
| JP | 2011-174939 | A | 9/2011 |
| JP | 2011-188860 | A | 9/2011 |
| JP | 2012-014066 | A | 1/2012 |
| WO | WO 2005/022113 | A2 | 3/2005 |
| WO | WO 2011/122200 | A1 | 10/2011 |
| WO | WO 2011/132584 | A1 | 10/2011 |

OTHER PUBLICATIONS

International Search Report and English translation thereof dated Dec. 16, 2014 in connection with International Application No. PCT/JP2014/004804.

Written Opinion and English translation thereof dated Dec. 16, 2014 in connection with International Application No. PCT/JP2014/004804.

International Preliminary Report on Patentability and English translation thereof dated Jul. 9, 2015 in connection with Application No. PCT/JP2013/006646.

International Preliminary Report on Patentability and English translation thereof dated May 19, 2016 in connection with International Application No. PCT/JP2014/004804.

Chinese Office Action and English Translation thereof dated Aug. 24, 2016 in connection with Chinese Application No. 2013800671457.

Chinese Office Action and English Translation thereof dated Mar. 20, 2017 in connection with Chinese Application No. 2013800671457.

Chinese Office Action and English Translation thereof dated Mar. 21, 2017 in connection with Chinese Application No. 2014800595299.

Extended European Search Report dated Mar. 28, 2017 in connection with European Application No. 14859938.4.

Japanese Office Action dated Jul. 25, 2017 in connection with Japanese Application No. 2014-554085 and English translation thereof.

Japanese Office Action dated Jul. 31, 2018 in connection with Japanese Application No. 2015-546279 and English translation thereof.

Betzig et al., Imaging Intracellular Fluorescent Proteins at Nanometer Resolution, Science, Sep. 15, 2006, vol. 313, pp. 1642-1645.

Crane et al., Determinants of aquaporin-4 assembly in orthogonal arrays revealed by live-cell single-molecule fluorescence imaging, Journal of Cell Science, 2009, vol. 122, No. 6, pp. 813-821.

Hayakawa et al., Intercellular network evaluation of the cardiac muscle cell. Regenerative Medicine. Feb. 1, 2011;10(Suppl):258.

Kunihiro et al., Examination of the heartbeat evaluation technique of the cultured cardiac muscle cell by the animated image analysis. Regenerative Medicine. Feb. 1, 2011;10(Suppl):144.

Oshima et al., Efficacy of motion analysis and visualization of neural cell for functional assessment, The Journal of Toxicological Sciences, Jun. 2013, vol. 38, No. Supplement, pS292.

Oshima et al., The three-dimensional information acquisition method of the viable cell using the Z-Stack animation image with the optical microscope. Bioimaging. Aug. 1, 2012;21(2):2010-211.

Rossi et al., Super-resolution imaging of aquaporin-4 orthogonal arrays of particles in cell membranes, J of Cell Science 125(18), pp. 4405-4412.

Uno et al., Development of new drug evaluation technique for the cardiac function by the animated image analysis. Japanese Association of Cardiovascular Pharmacology Koen Yoshishu. Dec. 2, 2012;21:47.

Yamamura et al., New light on ion channel imaging by total internal reflection fluorescence (TIRF) microscopy, Journal of Pharmacological Sciences, 2015, vol. 128, pp. 1-7.

Yamamura, Imaging analysis of ion channel molecule functions, Folia Pharmacologica Japonica, Aug. 9, 2013, vol. 142, No. 2, pp. 79-84.

Yamamura, Imaging analyses of ion channel molecule functions, Journal of Pharmacological Science, Mar. 15, 2013, vol. 121, No. Supplement 1, p. 10.

Japanese Office Action dated Jan. 8, 2019 in connection with Japanese Application No. 2015-546279 and English translation thereof.

Evans, J. J., An image processing technique for measuring the dynamic movement of cell membranes, Computers in Biology and Medicine, 2008, vol. 38, pp. 545-554 and Corrigendum pp. 941-943.

\* cited by examiner

CELL ANALYSIS SYSTEM, CELL ANALYSIS PROGRAM AND CELL ANALYSIS METHOD

CROSS REFERENCE TO RELATED APPLICATIONS

This application is a continuation of and claims the benefit under 35 U.S.C. § 120 of U.S. Patent application Ser. No. 15/033,089, titled "CELL ANALYSIS SYSTEM, CELL ANALYSIS PROGRAM AND CELL ANALYSIS METHOD," filed on Apr. 28, 2016, now U.S. Pat. No. 10,163,203, which claims the benefit under 35 U.S.C. § 371 as a U.S. National Stage Entry of International Application No. PCT/JP2014/004804, filed in the Japanese Patent Office as a Receiving Office on Sep. 18, 2014, which claims priority to Japanese Patent Application Number JP2013-232444, filed in the Japanese Patent Office on Nov. 8, 2013, each of which is hereby incorporated by reference in its entirety.

TECHNICAL FIELD

The present disclosure relates to a cell analysis system, a cell analysis program and a cell analysis method suitable for analyzing the movement of ions or molecules across a cell membrane.

BACKGROUND ART

The movement of ions or molecules across a cell membrane (hereinafter referred to as "cell membrane ion transport") is involved in formation and alteration of membrane potential which is important for cell functions. The cell membrane ion transport is made by a particular molecule (protein) included in the cell membrane. Ion pumps are molecules which allow the ions to move by expending some energy; and ion channels are molecules which open and close depending on the membrane potential, or upon binding of a particular molecule, thereby allowing the ion transport to be made corresponding to the concentration difference between the outside and the inside of the cell membrane.

The cell membrane ion transport is very important for cell functions, and if it is possible to grasp the cell membrane ion transport, it may be applicable in various ways. For example, ion channels are important as targets of drug discovery. In the past, evaluations of cell membrane ion transport have been usually made by a method using a patch-clamp technique (see, for example, Patent Document 1) or a method of measuring extracellular electric fields (see, for example, Patent Document 2). Methods of measuring intracellular ion concentrations by using fluorescence staining (see, for example, Patent Documents 3 and 4) have also been used.

Patent Document 1: Japanese Patent Application Laid-open No. 2006-184207
Patent Document 2: Japanese Translation of PCT International Application Publication No. 2008-538287
Patent Document 3: Japanese Translation of PCT International Application Publication No. 2006-526389
Patent Document 4: Japanese Translation of PCT International Application Publication No. 2003-527113

DISCLOSURE OF THE INVENTION

Problem to be Solved by the Invention

However, with the methods using the patch-clamp technique or the extracellular electric fields, it is only possible to evaluate the movement of the ions by the ion channels or the like within the regions of the cell membrane which are in contact with electrodes for measurement. Because of this, spatial resolution would depend on the size and the number of the electrodes. Accordingly, in cases where the size of the electrode is large and the number of the electrodes is small, the spatial resolution becomes low; but in cases where the number of the electrodes is large, the device may need to have a complicated configuration.

A problem of artifacts (noise due to human factors) and a problem of discoloring of fluorescence may arise in the method using fluorescence staining. Thus, by the measuring methods in the past, it has been difficult to measure the cell membrane ion transport at high resolution and without staining.

Accordingly, an object of the present disclosure is to provide a cell analysis system, a cell analysis program and a cell analysis method suitable for analyzing the movement of ions or molecules across cell membranes.

Means for Solving the Problem

In order to solve the problems described above, a cell analysis system according to the present disclosure includes a motion information extracting unit and a motion characteristics calculating unit.

The motion information extracting unit extracts motion information arising from a movement of ions or molecules across a cell membrane, out of a cell image obtained from imaging a cell in time series.

The motion characteristics calculating unit calculates motion characteristics of the motion information.

In order to solve the problems described above, a cell analysis program according to the present disclosure operates an information processing apparatus as a motion information extracting unit and a motion characteristics calculating unit.

The motion information extracting unit extracts motion information arising from a movement of ions or molecules across a cell membrane, out of a cell image obtained from imaging a cell in time series.

The motion characteristics calculating unit calculates motion characteristics of the motion information.

In order to solve the problems described above, a cell analysis method according to the present disclosure includes extracting motion information arising from a movement of ions or molecules across a cell membrane, out of a cell image obtained from imaging a cell in time series, by the motion information extracting unit.

The motion characteristics calculating unit calculates motion characteristics of the motion information.

Effects of the Invention

As described above, according to the present disclosure, it makes it possible to provide a cell analysis system, a cell analysis program and a cell analysis method suitable for analyzing the movement of ions or molecules across cell membranes.

Note that the effects described above are not limitative; and any effect described herein may be an effect according to an embodiment of the present disclosure.

MODE(S) FOR CARRYING OUT THE INVENTION

Figure 1:
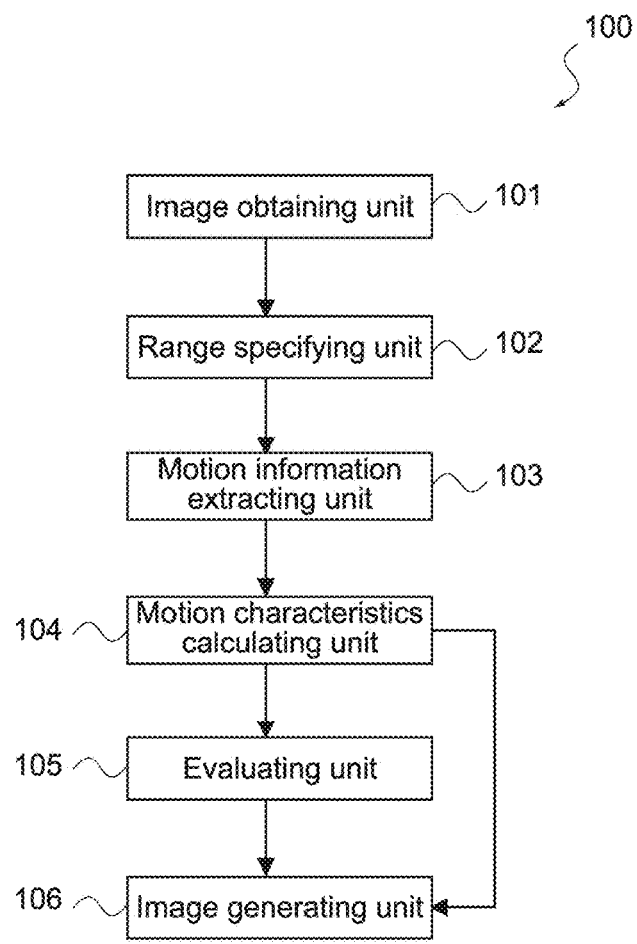
FIG. 1 A schematic diagram showing a configuration of a cell analysis system according to an embodiment of the present disclosure.

A cell analysis system according to the present disclosure includes a motion information extracting unit and a motion characteristics calculating unit.

The motion information extracting unit extracts motion information arising from a movement of ions or molecules across a cell membrane, out of a cell image obtained from imaging a cell in time series.

The motion characteristics calculating unit calculates motion characteristics of the motion information.

Since the cell membrane moves at an observable extent due to an inflow into the cell and an outflow out of the cell of the ions or the molecules, the information arising from the movement of the ions or the molecules is contained in the motion information that is to be extracted from the cell image. Accordingly, it becomes possible to evaluate the movement of the ions or the molecules across the cell membrane (hereinafter referred to as "cell membrane ion transport") based on the motion characteristics which is the characteristics of the motion information. The above-described configuration may eliminate the need of staining the cell. This makes it possible to prevent an influence on the cell of staining reagents. Furthermore, as the cell analysis system is able to evaluate the cell membrane ion transport by image processing to the cell image, it becomes possible to analyze a wide region at high resolution.

The cell analysis system may further include an image generating unit.

The image generating unit superposes the motion characteristics and the cell image, and generates a motion characteristics displaying image.

With this configuration, the cell analysis system is able to display the motion characteristics in an easily comprehensible form for a user. This allows the user to evaluate the movement of the ions or the molecules across the cell membrane by referring to the motion characteristics displaying image.

The cell analysis system may further include an evaluating unit.

The evaluating unit evaluates the movement of the ions or the molecules across the cell membrane, on the basis of the motion characteristics.

As described above, since the information arising from the movement of the ions or the molecules is contained in the motion information, the evaluating unit is able to evaluate the movement of the ions or the molecules across the cell membrane, on the basis of the motion characteristics.

The motion characteristics calculating unit may calculate a motion amount as the motion characteristics.

The evaluating unit may evaluate an amount of moved ions or molecules, on the basis of the motion amount.

The motion amount increases and decreases depending on an inflow amount of the ions or the molecules into the cell and an outflow amount of the ions or the molecules out of the cell. Accordingly, it becomes possible to evaluate the amount of the moved ions or the molecules, on the basis of the motion amount.

The motion characteristics calculating unit may calculate a motion amount as the motion characteristics.

The evaluating unit may evaluate an activity of an ion channel or an ionotropic receptor, on the basis of the motion amount.

Since the motion amount is to be increased and decreased depending on an inflow amount of the ions or the molecules into the cell and an outflow amount of the ions or the molecules out of the cell, it becomes possible to evaluate the activity of the ion channel or the ionotropic receptor, on the basis of the motion amount.

The motion characteristics calculating unit may calculate as the motion characteristics a change in a movement before and after addition of an activator or an inhibitor of an ion channel or an ionotropic receptor.

The evaluating unit may evaluate the presence or absence, or an amount, of the ion channel or the ionotropic receptor, on the basis of the change in the movement.

When an activator or an inhibitor of an ion channel or an ionotropic receptor is added to a cell, the ion channel or the ionotropic receptor is to be blocked or otherwise activated. As a result, the inflow amount of the ions or the molecules into the cell or the outflow amount of the ions or the molecules out of the cell would be changed. Accordingly, the movement of the cell membrane would be changed. Hence, it becomes possible to evaluate the presence or absence, or an amount, of the ion channel or the ionotropic receptor, on the basis of the change in the movement.

The motion characteristics calculating unit may calculate as the motion characteristics a change in a movement before and after addition of an inhibitor of an ionotropic receptor.

The evaluating unit may evaluate a type or a strength of a synapse formed between cells, on the basis of the change in the movement.

A synapse (intercellular junction) formed between cells stimulates the connected cell by using a particular chemical substance (neurotransmitter substance), thereby transmitting a signal to the connected cell. Accordingly, if the movement of the neurotransmitter substance across the cell membrane is reduced by an addition of an inhibitor of a receptor for a particular neurotransmitter substance, it can be evaluated that the synapse which uses the particular neurotransmitter substance has been formed. Since the movement of the neurotransmitter substance across the cell membrane is to be reflected in the movement of the cell membrane, it becomes possible to evaluate the type or the strength of the synapse formed between the cells, on the basis of the change in the movement before and after the addition of the inhibitor.

The motion characteristics calculating unit may calculate a motion amount as the motion characteristics.

The evaluating unit may evaluate a type or an effectiveness of a substance that acts on an ion channel or an ionotropic receptor, on the basis of the motion amount.

In such a manner as described above, the movement of the ions across the ion channel or the ionotropic receptor can be evaluated based on the motion amount. Hence, it becomes possible to evaluate the type or the effectiveness of the substance that acts on the ion channel or the ionotropic receptor, on the basis of the motion amount when the particular substance is added to the cell.

The motion characteristics calculating unit may calculate a motion amount as the motion characteristics.

The evaluating unit may evaluate a movement, a swell, a shrink and a vibration of the cell membrane due to a movement of ions across the cell membrane or a movement of water involved, on the basis of the motion amount.

The cell membrane swells when the ions or the water flows into the cell; and the cell membrane shrinks when the ions or the water flows out of the cell. In addition, by a repetition of the inflow and the outflow of the ions or the water in a short time, the cell membrane vibrates. As these movements of the cell membranes are reflected in the motion amount, it becomes possible to evaluate the movement, the swell, the shrink and the vibration of the cell membrane due to the movement of the ions or the water, on the basis of the motion amount.

The motion characteristics calculating unit may calculate a motion direction as the motion characteristics.

The motion characteristics calculating unit may evaluate a flow direction of the ions or the molecules across the cell membrane, on the basis of the motion direction.

Since the motion information of the cell image includes the information of the direction of the movement, it becomes possible to evaluate whether the ions or the molecules are flowing into the cell or flowing out of the cell, on the basis of the motion amount in terms of a particular motion direction.

The motion characteristics calculating unit may calculate a duration time or a spatial distribution of a movement.

The evaluating unit may evaluate a migration time of the ions or the molecules across the cell membrane or a spatial distribution of the ions or the molecules, on the basis of the duration time or the spatial distribution of the movement.

As described above, since a movement in the cell image occurs due to the movement of the ions or the molecules across the cell membrane, it is possible to regard the duration time of the movement as the migration time of the ions or the molecules; and it is possible to estimate the spatial distribution of the ions or the molecules from the spatial distribution of the movement.

The cell analysis system may further include a range specifying unit. The range specifying unit specifies an extraction range in the cell image by using a luminance difference in the cell image.

The motion information extracting unit may extract the motion information out of the extraction range.

In cases where the cell contained in the cell image is a neural cell, as the luminance of the cell body of the neural cell differs substantially from that of the nerve process of the neural cell, it is possible to detect the cell body and set it in the extraction range, by using the luminance difference. Accordingly, with the configuration described above, it becomes possible to calculate the motion characteristics with only the cell body set for the extraction range, and to use the cell body for the evaluation.

A cell analysis program according to the present disclosure operates an information processing apparatus as a motion information extracting unit and a motion characteristics calculating unit.

The motion information extracting unit extracts motion information arising from a movement of ions or molecules across a cell membrane, out of a cell image obtained from imaging a cell in time series.

The motion characteristics calculating unit calculates motion characteristics of the motion information.

A cell analysis method according to the present disclosure includes extracting motion information arising from a movement of ions or molecules across a cell membrane, out of a cell image obtained from imaging a cell in time series, by the motion information extracting unit.

The motion characteristics calculating unit calculates motion characteristics of the motion information.

A cell analysis system according to an embodiment will be described.

[Configuration of Cell Analysis System]

FIG. 1 is a schematic diagram showing a cell analysis system 100 according to the embodiment. As shown in the figure, the cell analysis system has an image obtaining unit 101, a range specifying unit 102, motion information extracting unit 103, a motion characteristics calculating unit 104, an evaluating unit 105 and an image generating unit 106. These configurations are functional configurations implemented as an information processing apparatus.

The image obtaining unit 101 obtains a "cell image". The cell image is an image obtained from imaging in time series a cell or a cluster of cells as a target for analysis. The cell image may be a video image; or the cell image may include a plurality of still images that have been successively imaged. The speed of imaging may be, for example, 1 to 30 fps (frame/second). Specifically, the cell image may be images obtained from imaging with the use of any of a variety of optical imaging techniques such as bright-field imaging, dark-field imaging, phase-contrast imaging, fluorescence imaging, confocal imaging, multiphoton-excited fluorescence imaging, absorbed light imaging and scattered light imaging.

Figure 2:
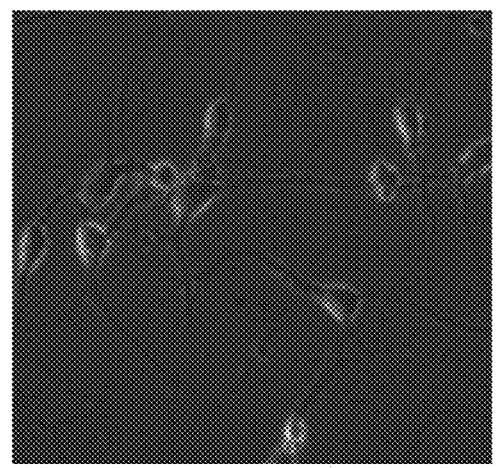
FIG. 2 An example of a cell image obtained by an image obtaining unit of the cell analysis system.

FIG. 2 is an example of the cell image, and it is an image containing a plurality of neural cells. The image obtaining unit 101 may obtain the cell image from an imaging apparatus (photomicroscopic apparatus) (not shown); or may also obtain, as the cell image, an image stored in storage or an image supplied from network. The image obtaining unit 101 supplies the obtained cell image to the range specifying unit 102.

Figure 3:
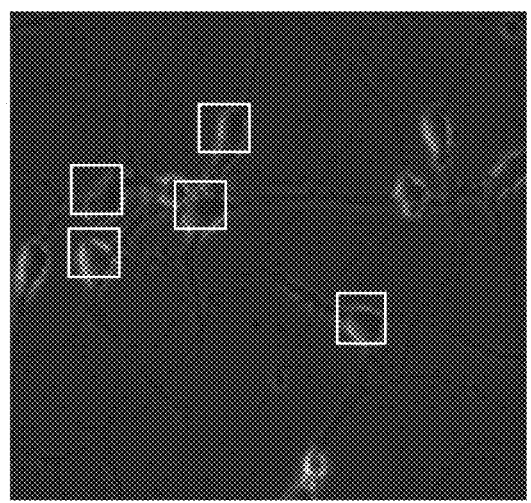
FIG. 3 An example of an extraction range to be specified by an extraction range specifying unit.

The range specifying unit 102 specifies an "extraction range" in the cell image. The extraction range is a range at which the motion information extracting unit 103, which is to be described later, extracts motion information. FIG. 3 is an example of the extraction range (in a square frame in the figure) which has been specified by the range specifying unit 102, in the cell image. The range specifying unit 102 is capable of setting the extraction range to the specified range in accordance with the target for analysis (a single cell, a cluster of cells, etc.) instructed by the user.

Specifically, in cases such as when the cell image includes only the cell or the cluster of cells as a target for analysis, it is possible to make the range specifying unit 102 specify the whole cell image as the extraction range. In cases where the cell image contains cells or clusters of cells other than the target for analysis, it is possible to make the range specifying unit 102 specify only a range of a part of the cell image as the extraction range.

The range specifying unit 102 may specify the extraction range by receiving an input of the instruction of the user, or may specify the extraction range by detecting the cell by image processing. The range specifying unit 102 is able to detect the cell by using a luminance difference in the cell image. In cases where the cell contained in the cell image is a neural cell, as the luminance of the cell body of the neural cell differs substantially from that of the nerve process of the neural cell, it is possible to detect the cell body and set it in the extraction range, by using the luminance difference. The range specifying unit 102 supplies the cell image and the specified extraction range to the motion information extracting unit 103.

The motion information extracting unit 103 extracts "motion information" out of the extraction range that has been specified by the range specifying unit 102. The motion information is information of a movement in the cell image that has been imaged in time series. Specifically, the motion information may be motion vectors of feature points in the cell image, following the time course. The motion information extracting unit 103 is able to extract the motion information by image processing such as block matching of the cell image.

Figure 4:
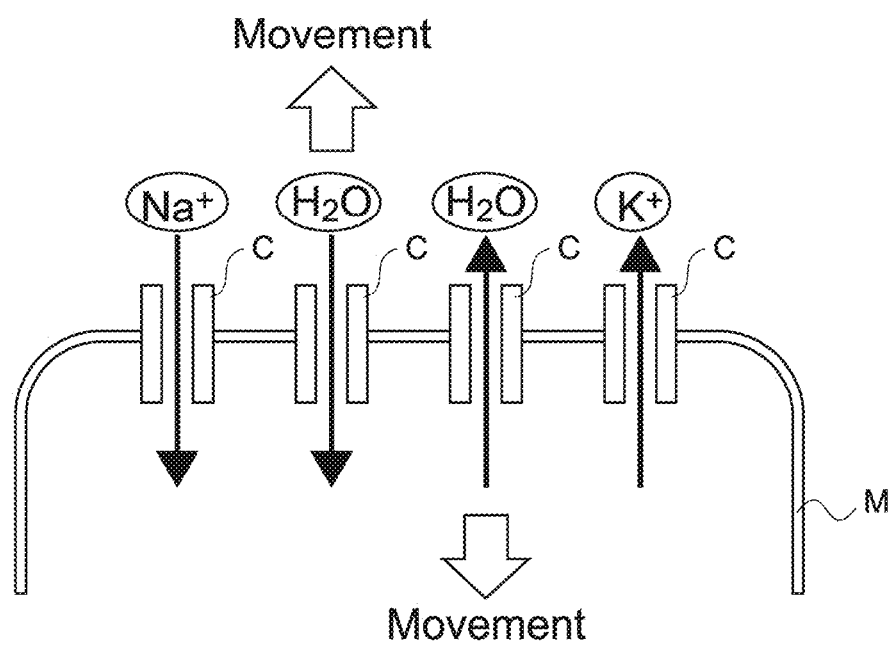
FIG. 4 A schematic diagram showing a movement of ions or molecules across a cell membrane.

The movement in the cell image arises from a movement of ions or molecules across a cell membrane (hereinafter referred to as "cell membrane ion transport"). FIG. 4 is a schematic diagram of a cell membrane ion transport. As shown in the figure, an ion ($K^+$, $Na^+$, etc.) or a molecule ($H_2O$, etc.) flows into the cell from the outside of the cell, or flows out of the cell from the inside of the cell, through a channel C of a cell membrane M.

Hereinafter, a structure responsible for the cell membrane ion transport such as an ion channel, a molecule channel, an ionotropic receptor, a molecule pump and an ion pump will be expressed as "ion channels and the like". The ions and the molecules that are to be transported by the ion channels and the like will be expressed as "ions and the like".

Now, the present inventors have found that a cell membrane moves at an observable extent due to the cell membrane ion transport. This is caused by swelling of the cell resulting from an inflow of the ions and the like into the cell, shrinking of the cell resulting from an outflow of the ions and the like out of the cell, or a vibration of the cell due to the inflow and the outflow of the ions and the like. Note that these movements are small and quick motions observed in a period of a few seconds or a shorter period, and are quite different from movements due to a migration of the cell itself observed in a period of a few hours. Thus, the motion information contains an effect of the cell membrane ion transport, so it becomes possible to evaluate the cell membrane ion transport by analyzing the motion information. The motion information extracting unit 103 supplies the extracted motion information to the motion characteristics calculating unit 104.

The motion characteristics calculating unit 104 calculates "motion characteristics" from the motion information. The motion characteristics is characteristics of the motion information, and is a variety of characteristics which can be calculated from the motion information such as a speed of the movement, a motion amount, a change in the movement, a motion direction, a duration time of the movement, a spatial distribution of the movement, a rate of suppression of the movement and an amount of the region containing the movement. Note that the "amount of the region containing the movement" is a proportion of a region in which the motion amount is equal to or more than a given amount, out of a region in the extraction range in which the cell is contained. The motion characteristics may also include an average value thereof in the extraction range and a median value thereof in a given time.

With an activator or an inhibitor of the ion channels and the like being added to the cell in an imaging time of the cell image, the motion characteristics calculation unit 104 is able to calculate as the motion characteristics a change in the movement before and after the addition of the activator or the inhibitor. Specifically, the motion characteristics calculation unit 104 is able to calculate as the motion characteristics a change in the speed of the movement, the motion amount, the motion direction, the spatial distribution of the movement, the amount of the region containing the movement, or the like, before and after the addition of the activator or the inhibitor.

Figure 5:
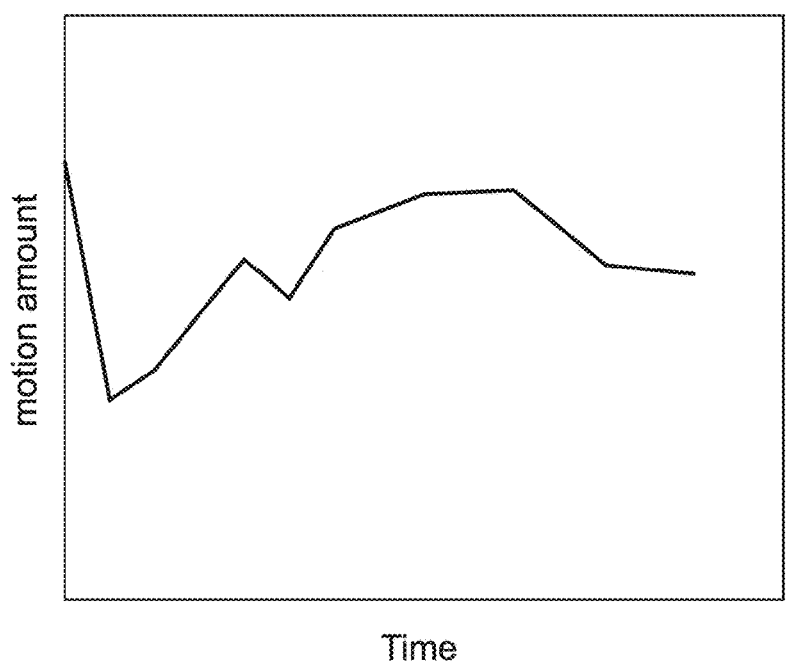
FIG. 5 An example of motion characteristics to be calculated by a motion characteristics calculating unit of the cell analysis system.

FIG. 5 is a graph showing a time change of the motion amount which serves as one example of the motion characteristics. The ordinate indicates the motion amount, and the abscissa indicates the time (imaging time of the cell image). This figure illustrates the motion amount that has been calculated with respect to a cell to which a particular ion-channel blocker has been added, which exemplifies that the motion amount has been decreased from the time of the addition of the ion-channel blocker (on the extreme left of the abscissa). The motion characteristics calculation unit 104 may calculate such motion characteristics. Further, the motion characteristics calculation unit 104 may calculate a plurality of types of motion characteristics from the motion information. The motion information extracting unit 103 supplies the calculated motion characteristics to the evaluating unit 105. The motion information extracting unit 103 may supply the calculated motion characteristics also to the image generating unit 106.

The evaluating unit 105 evaluates the cell membrane ion transport on the basis of the motion characteristics. For example, in the case of FIG. 5, it can be understood from the decrease in the motion amount after the addition of the ion-channel blocker that the function of the ion channel is inhibited by the ion-channel blocker. It can be understood from an increase in the motion amount along with the time course that the function of the ion channel has gradually recovered. In addition to this, the evaluating unit 105 is able to evaluate the cell membrane ion transport, on the basis of a variety of motion characteristics.

Specifically, the evaluating unit 105 is able to evaluate an amount of the moved ions and the like, on the basis of the motion amount. Since the motion amount increases and decreases depending on an inflow amount of the ions and the like into the cell and an outflow amount thereof out of the cell, it is possible to evaluate the amount of the moved ions and the like, on the basis of the motion amount.

Further, the evaluating unit 105 is able to evaluate an activity of the ion channels and the like, on the basis of the motion amount. Since the motion amount increases and decreases depending on the inflow amount of the ions and the like into the cell and the outflow amount thereof out of the cell, it would be reflected in the motion amount if the ion channels and the like have high activity and the inflow amount or the outflow amount of the ions and the like is large. Hence, the evaluating unit 105 is capable of evaluating the activity of the ion channels and the like, on the basis of the motion amount.

Still further, the evaluating unit 105 is able to evaluate the presence or absence, or an amount, of the ion channels and the like, on the basis of the change in the movement before and after addition of an activator or an inhibitor of the ion channels and the like. When an activator or an inhibitor of the ion channels and the like is added to a cell, the channels and the like are to be blocked or otherwise activated. As a result, the inflow amount of the ions and the like into the cell or the outflow amount thereof out of the cell would be changed. Accordingly, the movement of the cell membrane would be changed. Hence, it becomes possible to evaluate the presence or absence, or an amount, of the ion channel or the ionotropic receptor, on the basis of the change in the movement.

Still further, the evaluating unit 105 is able to evaluate a type or a strength of a synapse formed between the cells, on the basis of the change in the movement before and after addition of an inhibitor of an ionotropic receptor. A synapse (intercellular junction) formed between the cells stimulates the connected cell by using a particular chemical substance (neurotransmitter substance), thereby transmitting a signal to the connected cell. Accordingly, if the movement of the neurotransmitter substance across the cell membrane is reduced by the addition of the inhibitor of the receptor for a particular neurotransmitter substance, it can be evaluated that the synapse which uses the particular neurotransmitter substance has been formed. Since the movement of the neurotransmitter substance across the cell membrane is to be reflected in the movement of the cell membrane, it is possible to evaluate the type or the strength of the synapse formed between the cells, on the basis of the change in the movement before and after the addition of the inhibitor.

Still further, the evaluating unit 105 is able to evaluate a type or an effectiveness of a substance that acts on the ion channels and the like, on the basis of the motion amount. Since the movement of the ions and the like across the ion channels and the like can be evaluated based on the motion amount, it is possible to evaluate the type or the effectiveness of the substance that acts on the ion channels and the like, on the basis of the motion amount when the particular substance is added to the cell.

Still further, the evaluating unit 105 is able to evaluate a movement, a swell, a shrink and a vibration of the cell membrane due to a movement of ions across the cell membrane or a movement of water involved, on the basis of the motion amount. The cell membrane swells when the ions and the like flow into the cell; and the cell membrane shrinks when the ions or the water flows out of the cell. In addition, by a repetition of the inflow and the outflow of the ions or the water in a short time, the cell membrane vibrates. Since these movements of the cell membrane are to be reflected in the motion amount, it is possible to evaluate the movement, the swell, the shrink and the vibration of the cell membrane due to the movement of the ions or the water, on the basis of the motion amount.

Still further, the evaluating unit 105 is able to evaluate a flow direction of the ions or the molecules across the cell membrane, on the basis of the motion direction. Since the motion amount in terms of a particular motion direction is made by a flow of the ions and the like which are moving in that direction, it is possible to evaluate whether the ions and the like are flowing into the cell or flowing out of the cell. For example, depending on whether or not the motion direction at a particular point on a cell body that has been detected as the extraction range is oriented toward the center point of the cell body, it is possible to evaluate whether the ions and the like have flown into the cell or have flown out of the cell.

Furthermore, the evaluating unit 105 is able to evaluate a migration time of the ions or the molecules across the cell membrane or a spatial distribution of the ions or the molecules, on the basis of the duration time or the spatial distribution of the movement. As described above, since a movement in the cell image occurs due to the cell membrane ion transport, it is possible to regard the duration time of the movement as the migration time of the ions or the molecules; and it is possible to estimate the spatial distribution of the movement of the ions, or the spatial distribution of the ion channels and the like, from the spatial distribution of the movement.

In such a manner as described above, the evaluating unit 105 is capable of evaluating the cell membrane ion transport on the basis of the motion characteristics. The evaluating unit 105 supplies a result of the evaluation to the image generating unit 106.

The image generating unit 106 generates an image indicating the result of the evaluation. At this time, the image generating unit 106 may generate an image indicating the motion characteristics (e.g., graph of FIG. 5) together with the result of the evaluation; or may generate an image which only shows the motion characteristics and leave the task of evaluating the cell membrane ion transport to the user.

In addition, the image generating unit 106 may superpose the motion characteristics and the cell image, and generate a motion characteristics displaying image. Specifically, the image generating unit 106 may be capable of putting colors or contrasts corresponding to levels of the motion characteristics and superposing them with the corresponding positions of the cell image, thereby generating the motion characteristics displaying image.

For example, by allowing the image generating unit 106 to provide a color-map indicating the rate of suppression of the movement due to the ion-channel blocker overlapped on the cell image, it can allow the user to evaluate whether or not the ion channels are expressed, or the expressed amount thereof, with respect to each of the cells. Further, by allowing the image generating unit 106 to provide the color-map indicating a rate of suppression of a movement due to an ionotropic receptor antagonist overlapped on the cell image, it can allow the user to evaluate types, intensities, and a spatial distribution of an input of a synapse formed by each of the cells.

The cell analysis system 100 has the above-described configuration. As described above, the cell analysis system 100 is capable of evaluating the cell membrane ion transport from the motion characteristics of the cell image. Therefore, by using the cell analysis system 100, the user may not need to subject the cell to staining, and it becomes possible to prevent an influence on the cell of staining reagents. Furthermore, as the cell analysis system 100 is able to evaluate the cell membrane ion transport by image processing to the cell image, it becomes possible to analyze a wide region at high resolution.

Specifically, by using the cell analysis system 100, it becomes possible to perform relative quantification of the activity of the ion channels and the like without staining; or to perform screening of physiologically active substances and reagents that act on the ion channels and the like, without staining, while performing relative quantification of the effect thereof. Furthermore, by performing relative quantification for whether or not the ion channels are expressed in each of the cells, or for the expressed amount thereof, it becomes possible to perform profiling of cell types, without staining.

In addition, in cases where the target for analysis is neural cells, by performing relative quantification for kinds of ionotropic receptors of synapses that make their input to each of the neural cells, and for the amounts of input thereof, it becomes possible to perform profiling of synaptic connections, without staining. Further, by performing relative quantification of the alteration of the cell membrane potential formed by the ion channel, without staining, it becomes possible to evaluate the state of the cells (state of cellular differentiation, freshness, etc.) depending on that.

EXAMPLES

Example 1: Evaluation of Movement of Ions by Potential-Dependent Ion Channels

A potential-dependent ion channel opens and closes depending on the membrane potential, and it is a molecule responsible for the movement of ions depending on a transmembrane ion gradient. In many of the neural cells, the membrane potentials oscillate and do not stand still; and the potential-dependent ion channels repeat opening and closing. An ion-channel blocker inhibits the opening and closing of the ion channels, and blocks the transmembrane movement of the ions.

On a microscope having a chamber, iPS cell-derived neural cells "iCell Neuron" (produced by Cellular Dynamics International, Inc.) were set. A video image of the cells, of 260 frames at object lens magnification 20× and at 7.5 fps (frame/second), was taken and was obtained as a cell image. A variety of ion-channel blockers were added to the cell culture. The ion-channel blocker was one of: TTX (tetrodotoxin) which is $Na^+$ channel blocker; TEA (tetraethylammonium) which is $K^+$ channel blocker; and Nifedipine which is $Ca^{2+}$ channel blocker.

Figure 6:
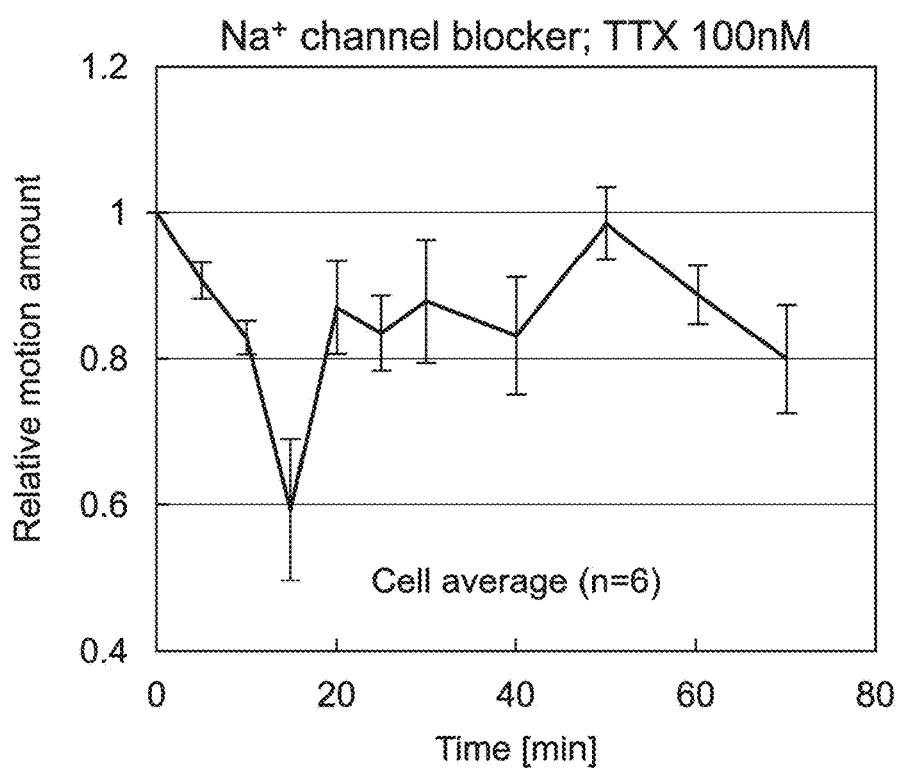
FIG. 6 A graph showing changes in a motion amount after adding $Na^+$ channel blocker to iPS cell-derived neural cells, according to Example 1 of the present disclosure.
Figure 7:
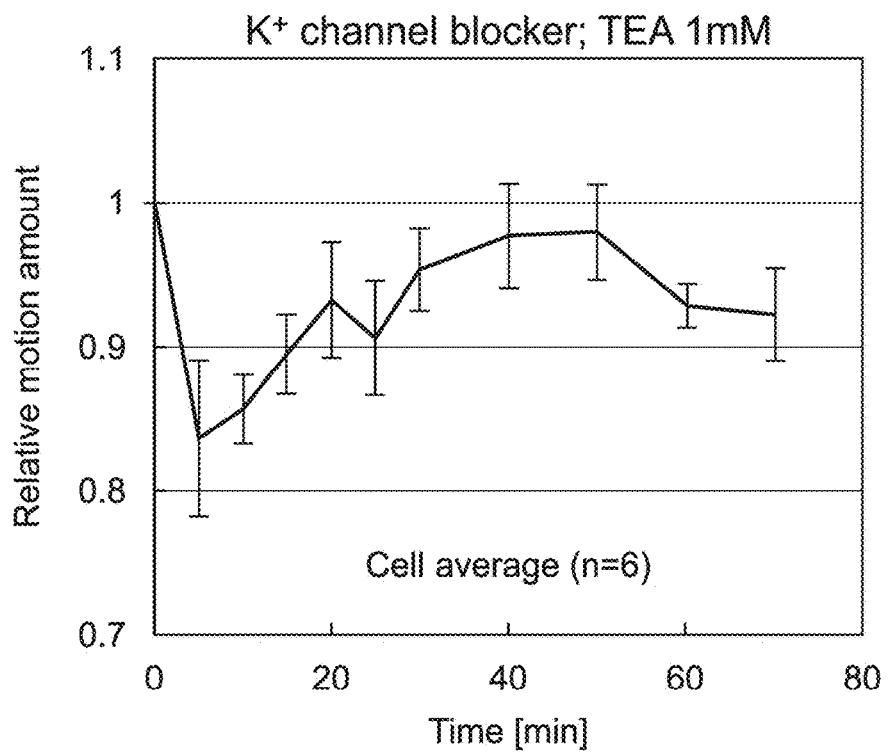
FIG. 7 A graph showing changes in a motion amount after adding $K^+$ channel blocker to iPS cell-derived neural cells, according to Example 1 of the present disclosure.
Figure 8:
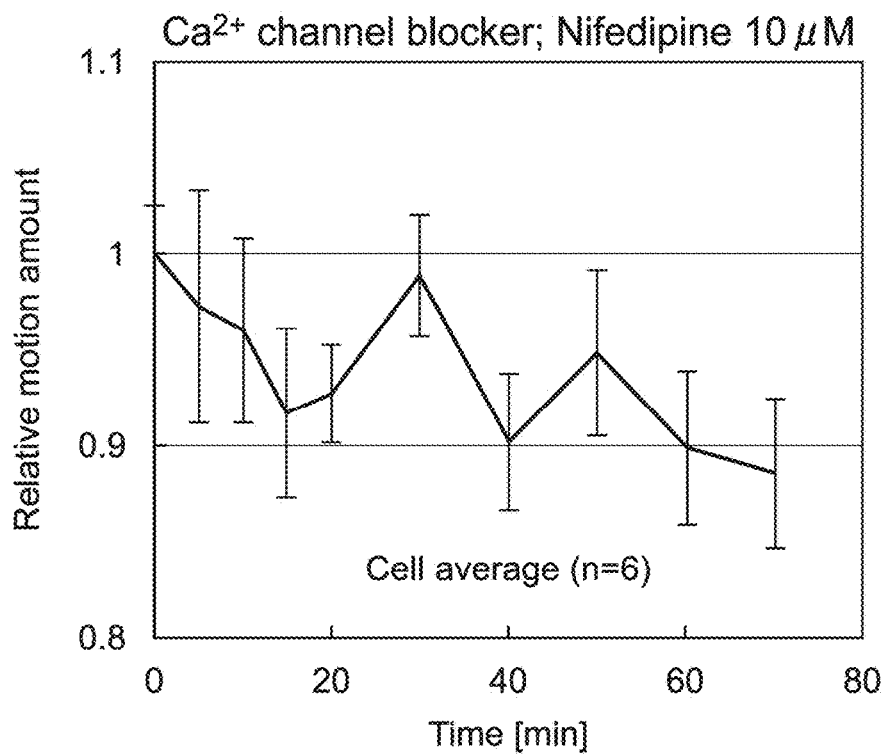
FIG. 8 A graph showing changes in a motion amount after adding $Ca^{2+}$ channel blocker to iPS cell-derived neural cells, according to Example 1 of the present disclosure.

The cell image was analyzed with the use of the above-described cell analysis system. Specifically, the motion information was extracted by block matching, using each of the neural cells in the cell image as the extraction range, and the motion amount (average of the speed of movement) was calculated from the motion information. FIGS. 6 to 8 are graphs showing results of the calculation of the motion amount. FIGS. 6, 7 and 8, respectively, were obtained from the calculation regarding a case where 100 nm of TTX was added to iCell Neuron, a case where 1 mM of TEA was added to iCell Neuron, and a case where 10 µM of Nifedipine was added to iCell Neuron. Note that the motion amounts shown in the respective figures are average values of the calculated motion amounts for a plurality (six pieces) of detail parts of nerves.

In each graph, "0 min" in the abscissa is the time of the addition of the ion-channel blocker, and the ordinate indicates a relative motion amount when the value before adding the ion-channel blocker (at 0 min) is assumed to be 1.

Each graph shown in FIGS. 6 to 8 showed a transient reduction of the motion amount after the addition of the ion-channel blocker. From this fact, it can be understood that by using the cell analysis system, it becomes possible to quantitatively measure the inhibition of the relative transmembrane movement of the ions, the inhibition resulting from the addition of the ion-channel blocker.

Example 2: Evaluation of Movement of Ions by Ionotropic Receptors

An ionotropic receptor opens and closes depending on binding of a ligand (substance that binds to the receptor) therefor, and it is a molecule responsible for the movement of ions depending on transmembrane ion concentrations. Many of the neurotransmitters serve as ligands for ionotropic receptors; and they are released from presynapses at axon tips of neural cells, to stimulate or suppress the corresponding neural cells synaptically connected thereto via receptors at postsynapses. Each neural cell releases only one kind of neurotransmitter; and one synapse may be involved to only a single neurotransmitter.

An ionotropic receptor antagonist inhibits the binding of the ligand to the ionotropic receptor and the opening and closing of the channel, and blocks the transmembrane movement of the ions at the membrane where the synapses have been formed.

On the microscope having the chamber, iPS cell-derived neural cells "iCell Neuron" (produced by Cellular Dynamics International, Inc.) and rat cerebral cortex primary culture (produced by Lonza, Inc.) were each set. Video images of the cells, of 260 frames at object lens magnification 20× and at 7.5 fps (for iCell Neuron) or 5 fps (for rat cerebral cortex primary culture), were taken and were obtained as cell images. A variety of ionotropic receptor antagonists were added to each of the cell cultures. The ionotropic receptor antagonist was Bicuculline which is GABA (gamma-aminobutyrate) receptor antagonist; or CNQX (6-cyano-7-nitroquinoxaline-2,3-dione) which is non-NMDA Glu (glutamate) receptor antagonist.

Figure 9:
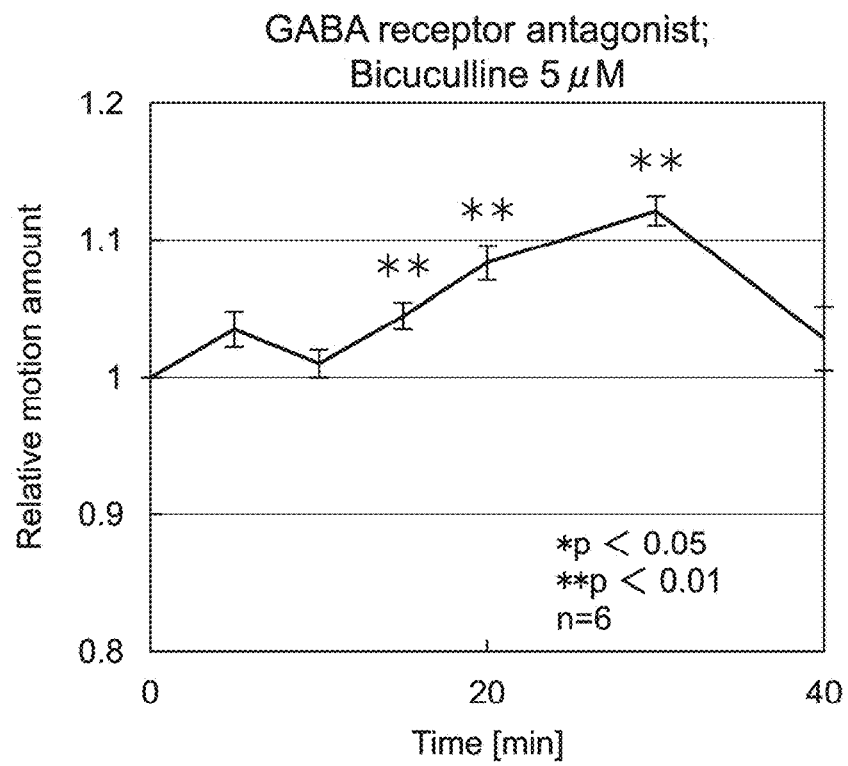
FIG. 9 A graph showing changes in a motion amount after adding GABA receptor antagonist to iPS cell-derived neural cells, according to Example 2 of the present disclosure.
Figure 10:
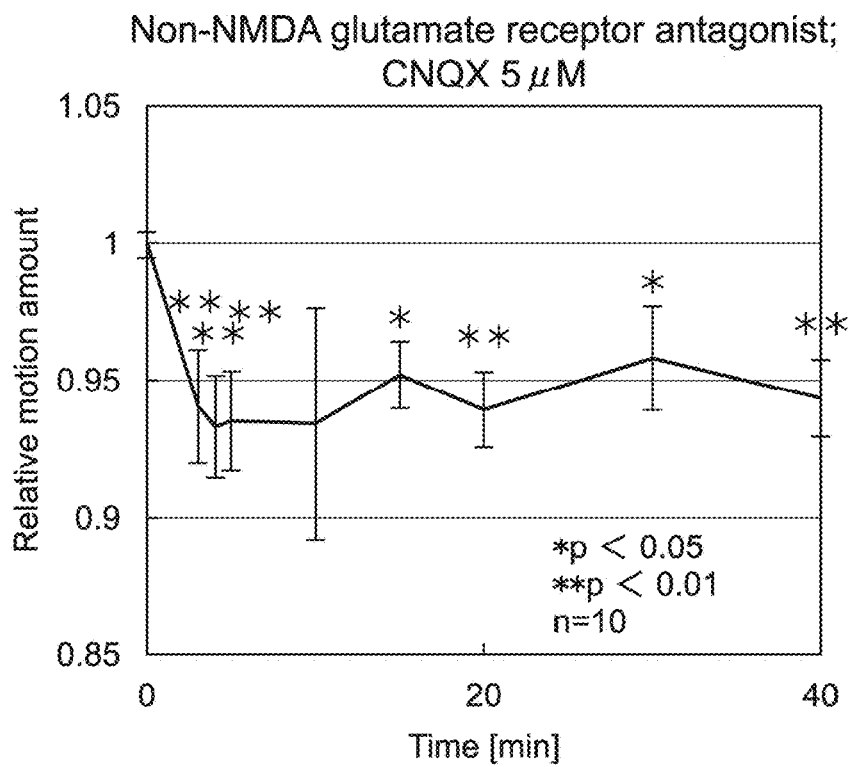
FIG. 10 A graph showing changes in a motion amount after adding Glu receptor antagonist to iPS cell-derived neural cells, according to Example 2 of the present disclosure.
Figure 11:
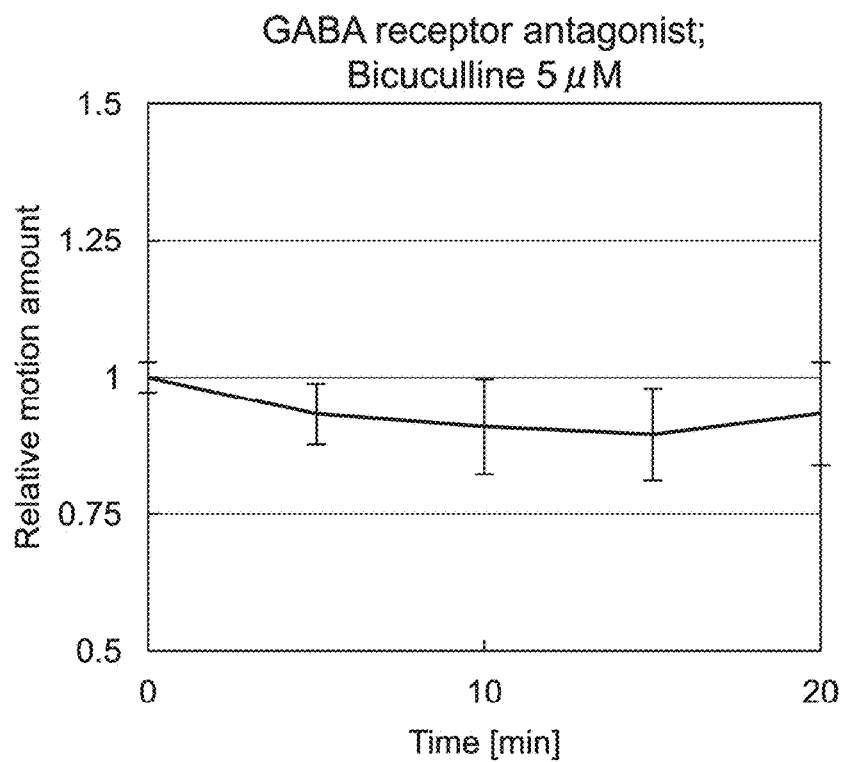
FIG. 11 A graph showing changes in a motion amount after adding GABA receptor antagonist to rat cerebral cortex neural cells, according to Example 2 of the present disclosure.
Figure 12:
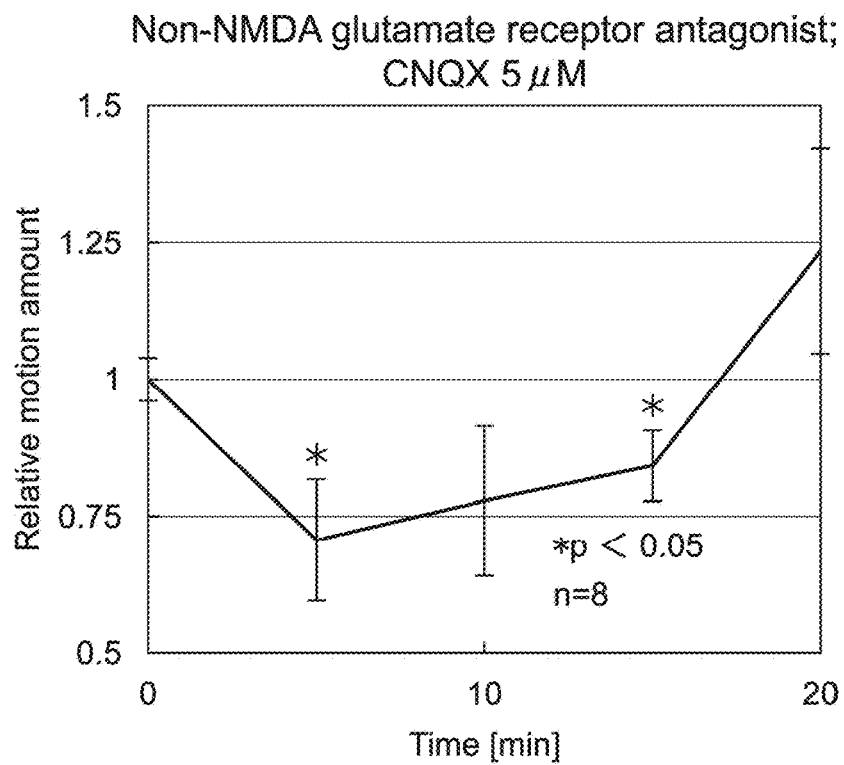
FIG. 12 A graph showing changes in a motion amount after adding Glu receptor antagonist to rat cerebral cortex neural cells, according to Example 2 of the present disclosure.

The cell image was analyzed with the use of the above-described cell analysis system. Specifically, the motion information was extracted by block matching, using each of the neural cells in the cell image as the extraction range, and the motion amount was calculated from the motion information. FIGS. 9 to 12 are graphs showing results of the calculation of the motion amount. FIGS. 9 and 10, respectively, were obtained from the calculation regarding a case where 5 µM of Bicuculline was added to iCell Neuron and a case where 5 µM of CNQX was added to iCell Neuron. FIGS. 11 and 12, respectively, were obtained from the calculation regarding a case where 5 µM of Bicuculline was added to rat cerebral cortex primary culture and a case where 5 µM of CNQX was added to rat cerebral cortex primary culture. Note that the motion amounts shown in the respective figures are average values of the calculated motion amounts for a plurality of detail parts of nerves.

In each graph, "0 min" in the abscissa is the time of the addition of the ion-channel blocker, and the ordinate indicates a relative motion amount when the value before adding the ionotropic receptor antagonist (at 0 min) is assumed to be 1.

In iCell Neuron, various cells that release neurotransmitter substances are mixed; and many of them are GABAergic neural cells or glutamatergic neural cells. As shown in FIG. 9, when the antagonist of the receptor for GABA was added to the iCell Neuron, GABA being an inhibitory neurotransmitter substance, the motion amount was transiently increased. As shown in FIG. 10, when the antagonist of the receptor for Glu (glutamate) was added to the iCell Neuron, Glu being an excitatory neurotransmitter substance, the motion amount was transiently reduced.

Therefore, from FIGS. 9 and 10, it is possible to grasp the fact that the synapses mediating GABA and the synapses mediating Glu were formed in the iCell Neuron. From the fact that a probability of synaptic transmission by spontaneous firing was increased by the GABA receptor antagonist and the probability thereof was decreased by the Glu receptor antagonist, it can be thought that the frequency of synaptic transmission was reflected in the motion amount.

In contrast, in the rat cerebral cortex primary culture, most of the cells thereof are glutamatergic neural cells, and almost no GABAergic neural cells are contained. Accordingly, by culturing the rat cerebral cortex primary culture, although the synapses mediating Glu may be formed, the synapses mediating GABA are not to be formed. In FIG. 11, there is little change in the motion amount by the addition of the GABA receptor antagonist, which indicates that the synapses mediating GABA were not formed. In FIG. 12, the motion amount is shown to have been decreased by the addition of the Glu receptor antagonist, which indicates that the synapses mediating Glu were formed. In this way, by using the cell analysis system, it is possible to evaluate whether or not the cell as the target of analysis has a receptor for a particular neurotransmitter substance.

Figure 13:
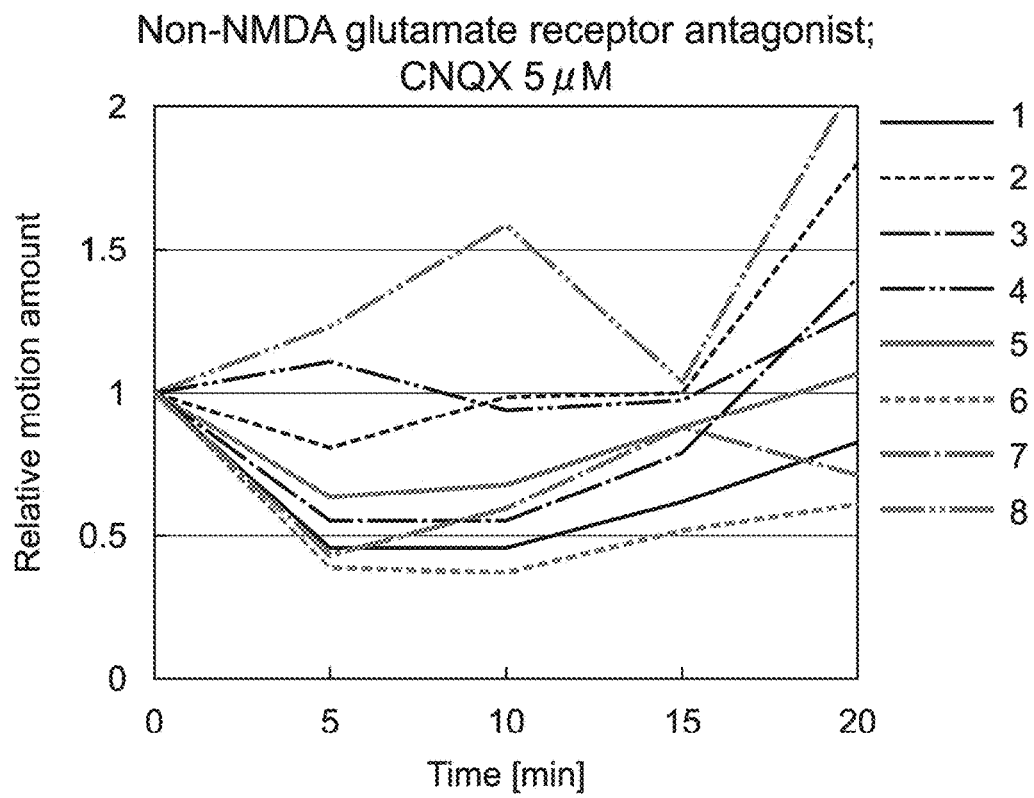
FIG. 13 A graph showing changes in a motion amount for each individual cell after adding Glu receptor antagonist to rat cerebral cortex neural cells, according to Example 2 of the present disclosure.

In addition, FIG. 13 is a graph obtained by plotting a motion amount for each individual cell after adding 5 μm of CNQX (Glu receptor antagonist) to the rat cerebral cortex primary culture. As shown in the figure, it can be understood that the rat cerebral cortex primary culture includes the cells in which the motion amount was decreased by an influence of the Glu receptor antagonist and the cells in which the motion amount was not decreased because there was no influence of the antagonist. Therefore, it can be said that, by using the cell analysis system, it is possible to evaluate whether or not the cell is one in which a synapse having a receptor for a particular neurotransmitter substance as an input was formed, with respect to each individual cell.

Example 3: Evaluation of Movement of Water by Change in Osmotic Pressure Associated with Transmembrane Movement of Ions Across the cell membrane, water migrates only through aquaporins which are water channels. An aquaporin opens and closes depending on an osmotic pressure difference, and it is a passive channel molecule responsible for the movement of water. When the osmotic pressure difference regarding the whole cell is produced between the inside and the outside of the cell, the aquaporins open; and the volume of the cell is increased or decreased. So far, it has not been found that the volume of the cell may be increased or decreased or the cell membrane may move because of a topical and transient osmotic pressure difference which is due to the opening and closing of ion channels or ionotropic receptors.

On the microscope having the chamber, rat cerebral cortex primary culture (produced by Lonza, Inc.) was set. A video image of the cells, of 260 frames at object lens magnification 20× and at 5 fps, was taken and was obtained as a cell image. To the cell culture, galactose at a final concentration of 2.5% was added.

Figure 14:
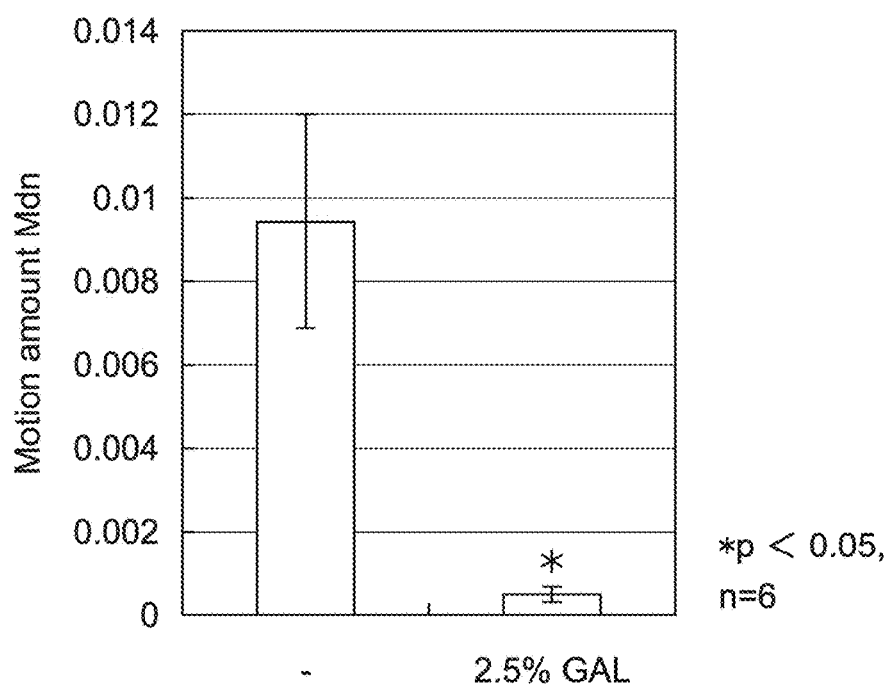
FIG. 14 A graph showing changes in a motion amount due to osmotic pressure in rat cerebral cortex neural cells, according to Example 3 of the present disclosure.

The cell image was analyzed with the use of the above-described cell analysis system. Specifically, the motion information was extracted by block matching, using each of the neural cells in the cell image as the extraction range, and the motion amount was calculated from the motion information. FIG. 14 shows a median value of the motion amounts for the extraction ranges. A graph on the left shows a value regarding a case where the galactose was not added; and a graph on the right shows a value regarding a case where the galactose was added.

As shown in the figure, in the case where the galactose was not added, a certain motion amount was produced by an inflow of $Na^+$ and $K^+$ into the cell and an outflow thereof out of the cell, and by the inflow and the outflow of water involved. When the galactose was added to this, thereby making the osmotic pressure outside the cell twice as large as the physiological concentration, the motion amount was almost completely reduced. This was because the inflow and the outflow of the ions were stopped due to a corruption of the physiological osmotic pressure, and because the movement of the water was stopped since the osmotic pressure difference was no longer present. Therefore, it can be understood that by using the cell analysis system, it becomes possible to evaluate the movement of water associated with the osmotic pressure difference between the inside and the outside of the cell.

Further, on the microscope having the chamber, rat cerebral cortex primary culture (produced by Lonza, Inc.) was set. A video image of the cells, of 260 frames at object lens magnification 20× and at 7.5 fps (for iCell Neuron) or 5 fps (for rat cerebral cortex primary culture), was taken and was obtained as a cell image. To the cell culture, 5 μm of $HgCl_2$ as aquaporin inhibitor was added.

Figure 15:
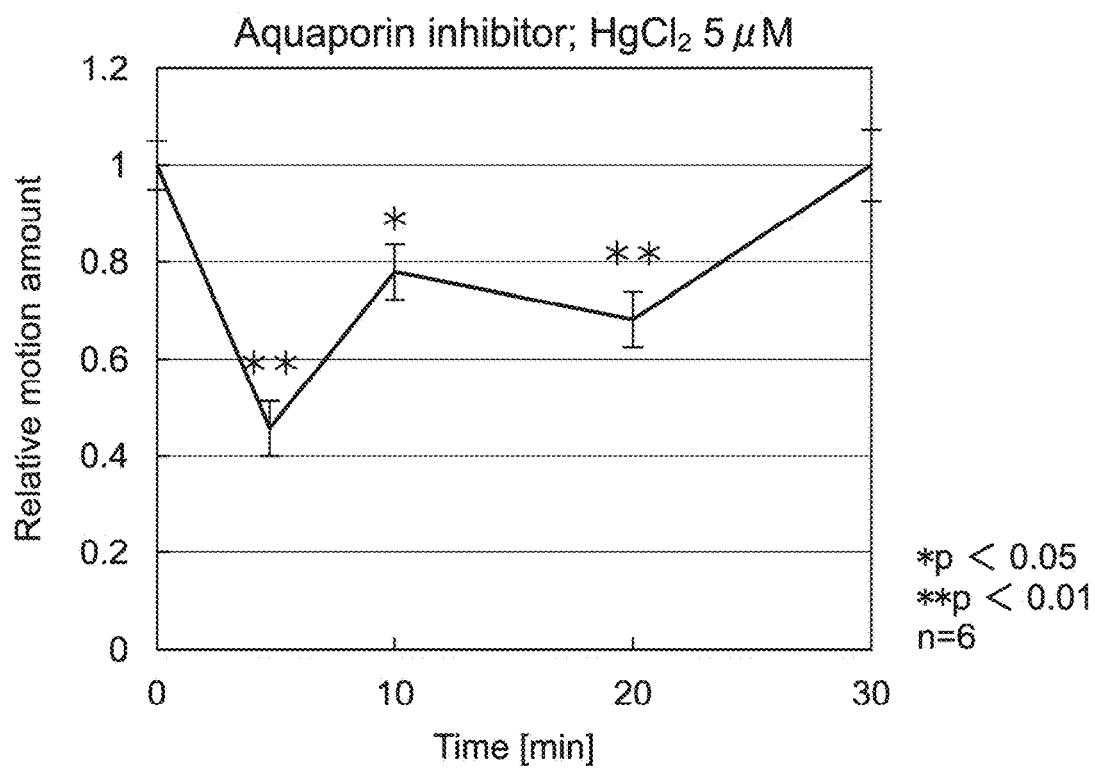
FIG. 15 A graph showing changes in a motion amount after adding aquaporin inhibitor to rat cerebral cortex neural cells, according to Example 3 of the present disclosure.

The cell image was analyzed with the use of the above-described cell analysis system. Specifically, the motion information was extracted by block matching, using each of the neural cells in the cell image as the extraction range, and the motion amount was calculated from the motion information. FIG. 15 is a graph showing a result of the calculation of the motion amount. In the figure, "0 min" in the abscissa is the time of the addition of the ion-channel blocker, and the ordinate indicates a relative motion amount when the value before adding $HgCl_2$ (at 0 min) is assumed to be 1.

As shown in the figure, when $HgCl_2$ was added to the rat cerebral cortex primary culture, $HgCl_2$ being an aquaporin inhibitor, the motion amount was transiently reduced. It should be noted that it had been confirmed that an addition of 5 μm of $HgCl_2$ does not inhibit metabolism of the cell. Accordingly, it was confirmed that when the movement of water across the cell membrane is inhibited by the aquaporin inhibitor, the movement in the cell would be inhibited. Therefore, it can be understood that by using the cell analysis system, it becomes possible to evaluate the movement of water across the cell membrane.

Example 4: Correlation of Motion Amounts and Extracellular Electric Fields

Figure 16:
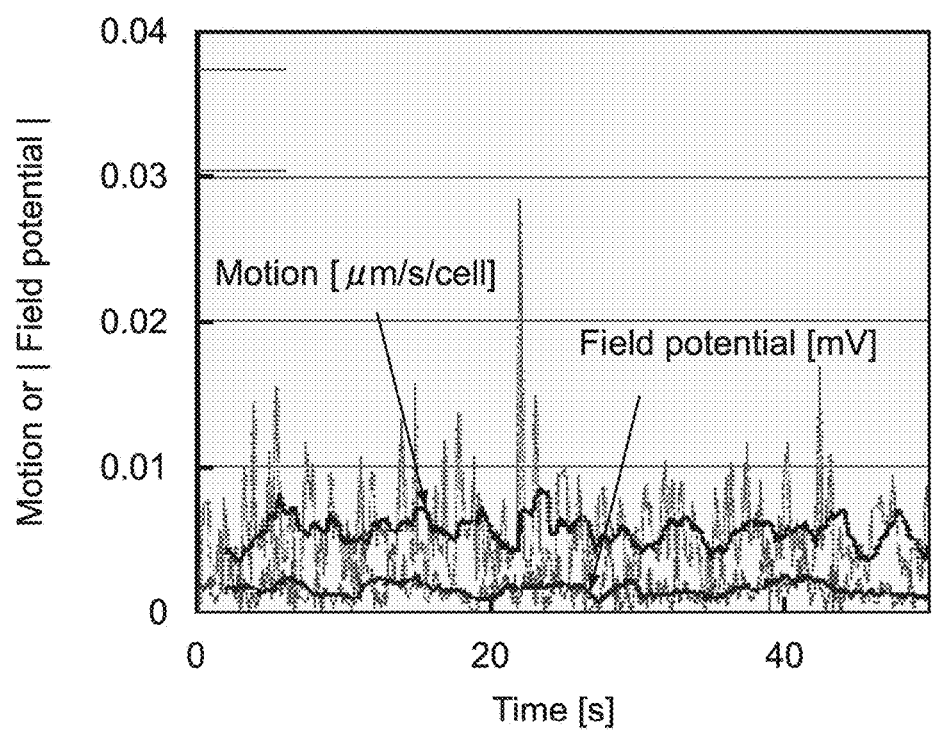
FIG. 16 A graph showing a result of measurement of motion amounts and extracellular electric fields, according to Example 4 of the present disclosure.

On a multielectrode array (produced by Alpha MED Scientific, Inc.), rat cerebral cortex primary culture (produced by Lonza, Inc.) was cultured. An extracellular electric field (field potential) was measured at a sampling frequency of 20 kHz. FIG. 16 shows the measured extracellular electric field. From the observed values, data for 200 Hz were extracted. After converting them to absolute values, an average thereof in 0.2 seconds (fine line of "Field potential" in FIG. 16) was taken and was obtained as data for 5 Hz.

A video image of the cells located along the electrodes, of 260 frames at 5 fps, was taken and was obtained as a cell image. The obtained cell image was analyzed with the use of the above-described cell analysis system. Specifically, the motion information was extracted by block matching, using each of the neural cells in the cell image as the extraction range, and an average of the speed of movement per one cell (fine line of "Motion" in FIG. 16) was calculated as the motion amount from the motion information.

Figure 17:
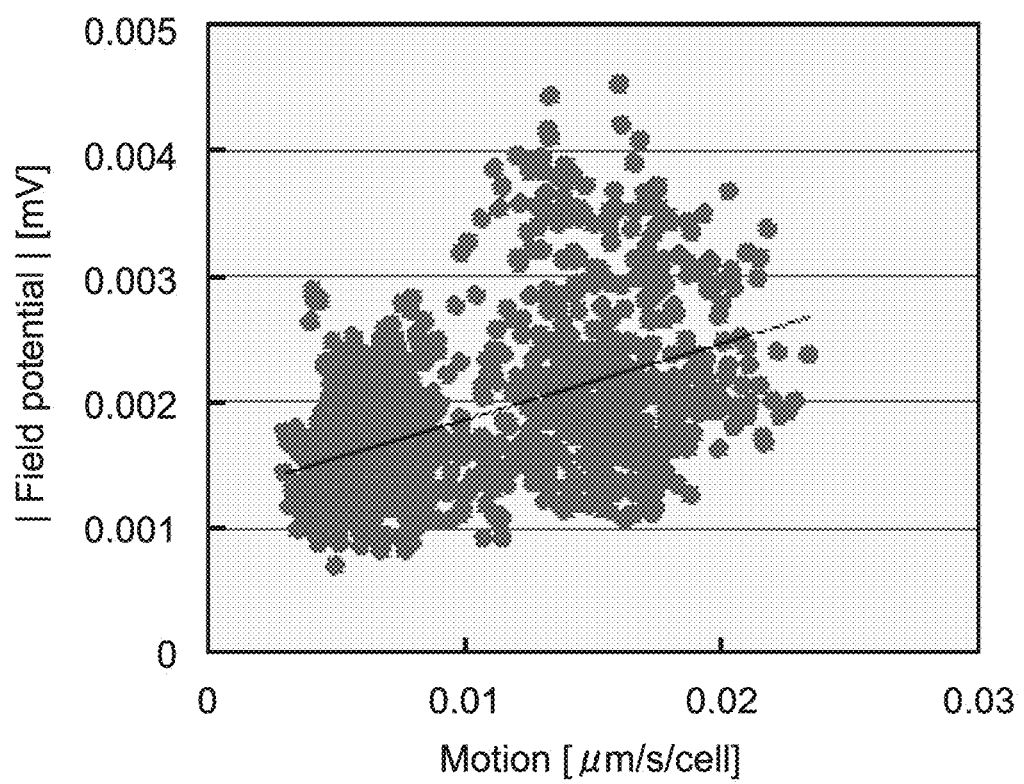
FIG. 17 A graph showing a correlation of motion amounts and extracellular electric fields, according to Example 4 of the present disclosure.

A moving average of the extracellular electric fields and that of the motion amounts for 10 intervals was calculated (thick lines of "Field potential" and "Motion" in FIG. 16). FIG. 17 is a graph showing a correlation of the moving average of the motion amounts and that of the extracellular electric fields shown in FIG. 16, obtained by plotting the values for same time points. As shown in the figure, it can be understood that a certain correlation was found between the extracellular electric fields and the motion amounts.

Example 5: Evaluation of Ion Inflow into Cells

On the microscope having the chamber, rat cerebral cortex primary culture (produced by Lonza, Inc.) was set. A video image of the cells, of 260 frames at object lens magnification 20× and at 5 fps, was taken and was obtained as a cell image. A culture solution used for the rat cerebral cortex primary culture was a normal culture solution, a HEPES buffer solution containing $Na^+$ (containing NaCl, KCl, $MgCl_2 CaCl_2$ and glucose) or a HEPES buffer solution without $Na^+$ (containing N-methyl-D-glucamine instead of NaCl). The HEPES buffer solution without $Na^+$ is one in which the osmotic pressure was adjusted by N-methyl-D-glucamine to the same extent as that of the HEPES buffer solution containing $Na^+$.

Figure 18:
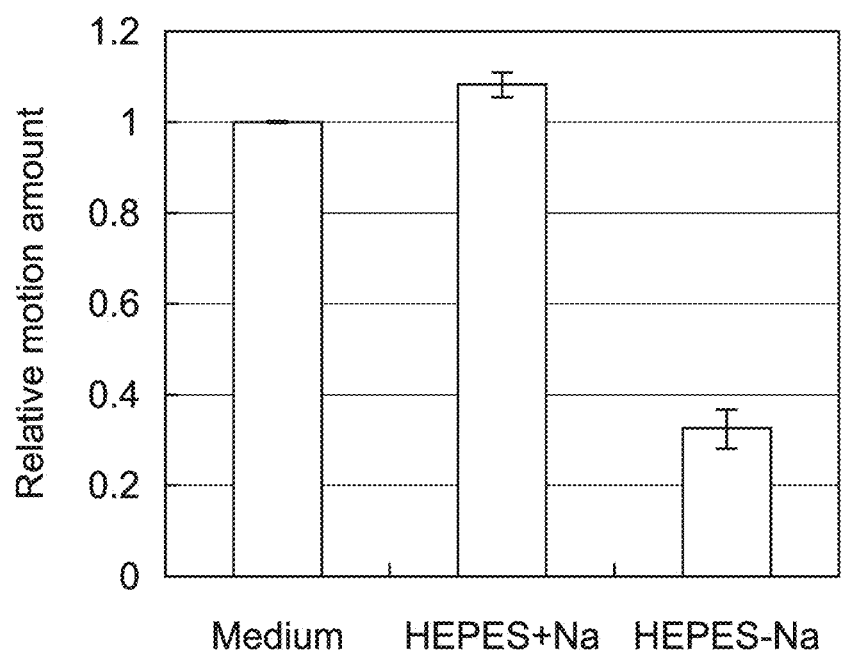
FIG. 18 A graph showing a difference of a motion amount depending on presence and absence of $Na^+$ ions in a cell culture liquid, according to Example 5 of the present disclosure.

The cell image was analyzed with the use of the above-described cell analysis system. Specifically, the motion information was extracted by block matching, using each of the neural cells in the cell image as the extraction range, and the motion amount was calculated from the motion information. FIG. 18 shows a median value of the motion amounts for the extraction ranges. Note that the motion amounts are normalized for each culture solution.

In the case where the culture solution was the HEPES buffer solution containing $Na^+$ ("HEPES+Na" in the figure), the motion amount was about the same as that of the case where it was the normal culture solution ("Medium" in the figure). On the other hand, in the case where the culture solution was the HEPES buffer solution without $Na^+$ ("HEPES-Na" in the figure), the motion amount was significantly decreased. From that fact, it can be said that the movement in the cell increased due to the inflow of $Na^+$ into the cell.

Note that the present disclosure may employ the following configurations.

(1) A cell analysis system including:
a motion information extracting unit to extract motion information arising from a movement of ions or molecules across a cell membrane, out of a cell image obtained from imaging a cell in time series; and
a motion characteristics calculating unit to calculate motion characteristics of the motion information.

(2) The cell analysis system according to (1), further including
an image generating unit to superpose the motion characteristics and the cell image, and generate a motion characteristics displaying image.

(3) The cell analysis system according to (1) or (2), further including
an evaluating unit to evaluate the movement of the ions or the molecules across the cell membrane, on the basis of the motion characteristics.

(4) The cell analysis system according to any one of (1) to (3), in which
the motion characteristics calculating unit calculates a motion amount as the motion characteristics, and
the evaluating unit evaluates an amount of moved ions or molecules, on the basis of the motion amount.

(5) The cell analysis system according to any one of (1) to (4), in which
the motion characteristics calculating unit calculates a motion amount as the motion characteristics, and
the evaluating unit evaluates an activity of an ion channel or an ionotropic receptor, on the basis of the motion amount.

(6) The cell analysis system according to any one of (1) to (5), in which
the motion characteristics calculating unit calculates as the motion characteristics a change in a movement before and after addition of an activator or an inhibitor of an ion channel or an ionotropic receptor, and
the evaluating unit evaluates the presence or absence, or an amount, of the ion channel or the ionotropic receptor, on the basis of the change in the movement.

(7) The cell analysis system according to any one of (1) to (6), in which
the motion characteristics calculating unit calculates as the motion characteristics a change in a movement before and after addition of an inhibitor of an ionotropic receptor, and
the evaluating unit evaluates a type or a strength of a synapse formed between cells, on the basis of the change in the movement.

(8) The cell analysis system according to any one of (1) to (7), in which
the motion characteristics calculating unit calculates a motion amount as the motion characteristics, and
the evaluating unit evaluates a type or an effectiveness of a substance that acts on an ion channel or an ionotropic receptor, on the basis of the motion amount.

(9) The cell analysis system according to any one of (1) to (8), in which
the motion characteristics calculating unit calculates a motion amount as the motion characteristics, and
the evaluating unit evaluates a movement, a swell, a shrink and a vibration of the cell membrane due to a movement of ions across the cell membrane or a movement of water involved, on the basis of the motion amount.

(10) The cell analysis system according to any one of (1) to (9), in which
the motion characteristics calculating unit calculates a motion direction as the motion characteristics, and
the motion characteristics calculating unit evaluates a flow direction of the ions or the molecules across the cell membrane, on the basis of the motion direction.

(11) The cell analysis system according to any one of (1) to (10), in which
the motion characteristics calculating unit calculates a duration time or a spatial distribution of a movement, and
an evaluating unit evaluates a migration time of the ions or the molecules across the cell membrane or a spatial distribution of the ions or the molecules, on the basis of the duration time or the spatial distribution of the movement.

(12) The cell analysis system according to any one of (1) to (11), further including
a range specifying unit to specify an extraction range in the cell image by using a luminance difference in the cell image;
the motion information extracting unit extracting the motion information out of the extraction range.

(13) A cell analysis program which operates an information processing apparatus as:
a motion information extracting unit extracting motion information arising from a movement of ions or molecules across a cell membrane, out of a cell image obtained from imaging a cell in time series; and
a motion characteristics calculating unit calculating motion characteristics of the motion information.

(14) A cell analysis method including:
extracting motion information arising from a movement of ions or molecules across a cell membrane, out of a cell image obtained from imaging a cell in time series, by a motion information extracting unit; and
calculating motion characteristics of the motion information by a motion characteristics calculating unit.

DESCRIPTION OF REFERENCE NUMERALS

100 cell analysis system
101 image obtaining unit
102 range specifying unit
103 motion information extracting unit
104 motion characteristics calculating unit
105 evaluating unit
106 image generating unit

The invention claimed is:
1. A cell analysis system comprising:
an imaging apparatus configured to capture a first cell image and a second cell image; and
a non-transitory computer-readable storage medium storing a cell analysis program which operates an information processing apparatus to execute:
extracting first motion information from the first cell image and second motion information from the second cell image, wherein the first cell image and the second cell image are obtained from imaging a cell in time series;
calculating a first motion characteristic from the first motion information and a second motion characteristic from the second motion information; and
evaluating a movement of at least one ion or molecule across a cell membrane of the cell based on a difference between the first motion characteristic and the second motion characteristic.

2. The cell analysis system according to claim 1, wherein the cell analysis program further operates the information processing apparatus to execute:
superposing the first motion characteristic and the first cell image, and generate a first motion characteristics displaying image.

3. The cell analysis system according to claim 1, wherein the cell analysis program further operates the information processing apparatus to execute:
superposing the second motion characteristic and the second cell image, and generate a second motion characteristics displaying image.

4. The cell analysis system according to claim 1, wherein the cell analysis program further operates the information processing apparatus to execute:
determining, based on the first motion characteristic and the second motion characteristic, one or more metrics relating to the movement of the at least one ion or molecule.

5. The cell analysis system according to claim 4, wherein the cell analysis program further operates the information processing apparatus to execute:
calculating a motion amount, and evaluate an amount of moved ions or molecules, on the basis of the motion amount.

6. The cell analysis system according to claim 4, wherein the cell analysis program further operates the information processing apparatus to execute:
calculating a motion amount, and evaluate an activity of an ion channel or an ionotropic receptor, on the basis of the motion amount.

7. The cell analysis system according to claim 4, wherein the cell analysis program further operates the information processing apparatus to execute:
calculating a change in the movement of the at least one ion or molecule before and after addition of an activator or an inhibitor of an ion channel or an ionotropic receptor, and evaluate the presence or absence, or an amount, of the ion channel or the ionotropic receptor, on the basis of the change in the movement of the at least one ion or molecule.

8. The cell analysis system according to claim 4, wherein the cell analysis program further operates the information processing apparatus to execute:
calculating a change in the movement of the at least one ion or molecule before and after addition of an inhibitor of an ionotropic receptor, and evaluate a type or a strength of a synapse formed between cells, on the basis of the change in the movement of the at least one ion or molecule.

9. The cell analysis system according to claim 4, wherein the cell analysis program further operates the information processing apparatus to execute:
calculating a motion amount, and evaluate a type or an effectiveness of a substance that acts on an ion channel or an ionotropic receptor, on the basis of the motion amount.

10. The cell analysis system according to claim 4, wherein the cell analysis program further operates the information processing apparatus to execute:
calculating a motion amount, and evaluate a movement, a swell, a shrink and a vibration of a cell membrane due to the movement of the at least one ion or molecule across the cell membrane or a movement of water involved, on the basis of the motion amount.

11. The cell analysis system according to claim 4, wherein the cell analysis program further operates the information processing apparatus to execute:
calculating a motion direction, and evaluate a flow direction of the at least one ion or molecule, on the basis of the motion direction.

12. The cell analysis system according to claim 4, wherein the cell analysis program further operates the information processing apparatus to execute:
  calculating a duration time or a spatial distribution of the movement of the at least one ion or molecule, and evaluate a migration time of the at least one ion or molecule across the cell membrane or a spatial distribution of the at least one ion or molecule, on the basis of the duration time or the spatial distribution of the movement of the at least one ion or molecule.

13. The cell analysis system according to claim 1, wherein the cell analysis program further operates the information processing apparatus to execute:
  specifying an extraction range in the first cell image by using a luminance difference in the first cell image, and extract the first motion information out of the extraction range.

14. The cell analysis system according to claim 1, wherein the cell analysis program further operates the information processing apparatus to execute:
  specifying an extraction range in the second cell image by using a luminance difference in the second cell image, and extract the second motion information out of the extraction range.

15. A non-transitory computer-readable storage medium storing a cell analysis program which operates an information processing apparatus to execute:
  extracting a first motion information from a first cell image and a second motion information from a second cell image, wherein the first cell image and the second cell image are obtained from imaging a cell in time series;
  calculating a first motion characteristic from the first motion information and a second motion characteristic from the second motion information; and
  evaluating a movement of at least one ion or molecule across a cell membrane of the cell based on a difference between the first motion characteristic and the second motion characteristic.

16. A cell analysis method comprising:
  extracting a first motion information from a first cell image and a second motion information from a second cell image, wherein the first cell image and the second cell image are obtained from imaging a cell in time series;
  calculating a first motion characteristic from the first motion information and a second motion characteristic from the second motion information; and
  evaluating a movement of at least one ion or molecule across a cell membrane of the cell based on a difference between the first motion characteristic and the second motion characteristic.

* * * * *